United States Patent [19]

Klein et al.

[11] Patent Number: 5,053,133

[45] Date of Patent: Oct. 1, 1991

[54] AFFINITY SEPARATION WITH ACTIVATED POLYAMIDE MICROPOROUS MEMBRANES

[76] Inventors: Elias Klein, 5517 Hempstead Rd.; Pamela A. Feldhoff, 301 Chelsea Rd., both of Louisville, Ky. 40207

[21] Appl. No.: 477,512

[22] Filed: Feb. 9, 1990

[51] Int. Cl.$^5$ .................... B01D 71/56; B01D 15/08
[52] U.S. Cl. .................... 210/500.38; 210/198.2
[58] Field of Search ............ 210/650, 656, 198.2, 210/500.38

[56] References Cited

U.S. PATENT DOCUMENTS

| | | | |
|---|---|---|---|
| 3,876,738 | 4/1975 | Marinaccio et al. | 264/41 |
| 3,959,079 | 5/1976 | Mareschi et al. | 210/656 X |
| 4,340,479 | 7/1982 | Pall | 210/490 |
| 4,340,480 | 7/1982 | Pall et al. | 210/490 |
| 4,415,631 | 11/1983 | Schutijser | 210/656 X |
| 4,478,914 | 10/1984 | Giese | 428/407 |
| 4,482,514 | 11/1984 | Schindler et al. | 264/41 |
| 4,584,103 | 4/1986 | Linder et al. | 210/650 |
| 4,595,503 | 6/1986 | Schindler et al. | 210/500.38 |
| 4,693,985 | 9/1987 | Degen et al. | 210/198.2 X |
| 4,702,840 | 10/1987 | Degen et al. | 210/638 |
| 4,707,266 | 11/1987 | Degen et al. | 210/638 |
| 4,727,034 | 2/1988 | Matsushita et al. | 210/656 X |
| 4,743,373 | 5/1988 | Rai et al. | 210/198.2 X |
| 4,794,088 | 12/1988 | Miyaki et al. | 210/198.2 X |
| 4,882,226 | 11/1989 | Schutyser et al. | 210/656 X |
| 4,883,598 | 11/1989 | Riethorst et al. | 210/656 |
| 4,889,636 | 12/1989 | Perry et al. | 210/500.38 X |
| 4,906,374 | 3/1990 | Gsell | 210/500.38 X |
| 4,906,379 | 3/1990 | Hodgins et al. | 210/500.38 X |
| 4,927,879 | 5/1990 | Pidgeon | 210/656 X |
| 4,931,498 | 6/1990 | Pidgeon | 210/656 X |

FOREIGN PATENT DOCUMENTS

| | | | |
|---|---|---|---|
| 60-209207 | 10/1985 | Japan | 210/500.38 |
| 61-025606 | 2/1986 | Japan | 210/500.38 |
| 63-287503 | 11/1988 | Japan | 210/500.38 |

*Primary Examiner*—Robert Spitzer
*Attorney, Agent, or Firm*—Hoffman, Wasson & Gitler

[57] ABSTRACT

Affinity membranes are prepared by activation of polyamide microporous films. In particular, the films are activated with 1,1'-carbonyldiimidazole, 2-fluoro-1-methylpyridinium$^{(+)}$ toluene-4-sulfonate$^{(-)}$, trichlorotriazine, or derivatives thereof, followed by binding of ligand to the activated sites. The polyamide microporous activated films include composite films comprising polyamide covalently bound to a polyhydroxyl compound such as a polysaccharide.

39 Claims, No Drawings

AFFINITY SEPARATION WITH ACTIVATED POLYAMIDE MICROPOROUS MEMBRANES

BACKGROUND OF THE INVENTION

Affinity purification ("affinity chromatography") broadly refers to separation methods based on a relatively high binding capacity ("affinity") of a target material to be purified, generally termed a "ligate", for a complementary ligand. While such purifications can be accomplished in solution, more typically, a ligand selected inter alia for selectivity toward the target material is immobilized on a supporting matrix; the mixture to be purified with respect to the ligate is then exposed to the matrix-bound ligand, and the resulting ligate/ligand complex is subsequently dissociated and the ligate recovered, if desired. The procedure has had particular application in the separation of biological materials, especially biological macromolecules such as proteins.

While biological purifications based on such affinity separations are relatively straightforward in theory, numerous problems have arisen in practice, particularly with respect to obtaining matrix systems adapted for rapid separation and optimum yield and purity of the target material. Ideally, matrices for ligand immobilization should have a large surface area and comprise an open and loose porous network to maximize interaction of matrix-bound ligand with ligate during the separation procedure. The matrix should be chemically and biologically inert, at the very least toward the ligand and ligate; be adapted for ligand immobilization; and be stable under reaction conditions employed, for example during matrix activation, ligand binding, and ligand-ligate complex formation, especially with respect to the solvent, pH, salt, and temperature employed. The matrix should also be stable for a reasonable length of time under ordinary storage conditions. To minimize competition for the target material and maximize purity of recovered product, supports for immobilization of ligands, especially biospecific ligands, should be free from extraneous ion exchange sites, and should not promote non-specific bonding. Matrices, especially those used in pressurized affinity separation techniques, should be mechanically strong and be able to withstand at least the moderate pressures typical of these conventional systems (up to about 5 bar, for example). Further, since matrices are frequently derivatized, for example to promote ligand immobilization or to permit improved ligand/target interaction, the matrix should be readily derivatizable to these ends, preferably at room temperature and in aqueous media, without the use of toxic chemicals; the derivatized matrix should also meet the above criteria.

A number of useful matrix materials have been identified over the years since the principles of affinity chromatography were first enunciated, including agarose gels; cellulose; dextran; polyacrylamide; hydroxyalkyl-methacrylate gels; polyacrylamide/agarose gels; ethylene copolymers, especially with polyvinyl acetate; copolymers of methacrylamide, methylene bis-methacrylamide, glycidyl-methacrylate and/or allyl-glycidyl-ether (such as Eupergit C, Rohm Pharma, Darmstadt, West Germany); and diol-bonded silica.

These and similar known matrix materials have been in the past typically coupled with the selected ligand and distributed in chromatographic columns in bead form. The material to be purified is then passed through the column; the target material is adsorbed by the beads, and, if desired, subsequently recovered by desorption of the ligate and elution from the column. Beads in current use commonly range in size from about 60 to about 300 mesh (U.S. standard), and accordingly must have adequate porosity to permit access of the target material to internally-bound ligands for efficient separation; preparation of beads of both good porosity and stability has proved difficult. Further, since chromatographic bead columns are susceptible to clogging with biological debris leading to rise in pressure and collapse of the beads, particulates must be pre-filtered from the material to be purified before affinity separation is undertaken; this often causes product loss, and in many instances (e.g., wherein the ligate is derived from a genetically-engineered microorganism), adequate removal of particulates from the crude preparation is difficult or impossible.

To overcome these problems, techniques have recently been developed employing microporous membranes or films rather than beads as the preferred matrix form for immobilizing ligands for affinity separations. In affinity separation systems employing microporous membranes, the crude filtration fluid containing the ligate flows through the membrane, typically under pressure, by convection processes which rapidly bring the ligate immediately into the vicinity of the affinity ligands immobilized on the membrane, in contrast to the much slower diffusion processes which characterize the crude fluid flow over matrices typical of the conventional bead chromotography separations described above. Additionally, owing to the large surface area of these membranes, the attached ligands have a high exposure to the ligates present in the material to be purified.

SUMMARY OF THE INVENTION

The invention provides an improved matrix for affinity separation comprising an activated polyamide microporous membrane for immobilization of ligands selected to complex with a target ligate. The membrane comprises a substantially inert aliphatic (i.e., non-aromatic) semicrystalline polyamide having an average pore size which retains solid materials or particulates present in the substrate fluid but which permits passage of solubilized materials, including target ligate materials, for maximum interaction of ligate with bound ligand and separation of particulates without a preliminary filtration step. Activation of the membrane according to the invention produces high product yields, low non-specific adsorption (resulting, for example, from introduction of extraneous charges on conventional membranes during processing), and formation of a very stable linkage between the selected ligand and the membrane. The matrix of the invention is particularly suitable for the separation of biological materials, particularly proteins, and especially for the recovery or removal of selected blood proteins such as pathological antigens or antibodies.

DETAILED DESCRIPTION OF THE INVENTION

1. Starting Material

Starting material for preparation of a matrix according to the invention comprises a microporous polyamide membrane or film which is activated as described below to react with and bind a ligand selected for affinity for the target ligate, or activated to provide an intermediate composite microporous membrane which is then in turn activated to react with and bind the selected ligand.

In general, useful starting polyamide membranes for activation according to the invention comprise film-forming aliphatic semicrystalline microporous polyamide films derived from polymers or copolymers of natural or synthetic polyamides wherein the aliphatic component typically contains up to about 20 carbon atoms and is branched or unbranched, saturated or unsaturated, substituted or unsubstituted, as well-understood in the art. The films have an average pore size sufficient to prevent throughput of particulate materials present in the material to be filtered, but which permits throughput of solubilized materials including target ligate; film average pore sizes of up to about $3\mu$, e.g., from about $0.6\mu$ to about $3\mu$, or more particularly from about $2\mu$ to $3\mu$, for example, are generally suitable for typical biological applications. Suitable starting membranes or films for activation according to the invention are substantially insoluble in the solvents to which they are exposed during activation, ligand binding, and/or use, particularly water and common organic solvents such as acetonitrile, acetone, ethers, hydrocarbons, or ketones, and exhibit substantial resistance to loss of pore structure, as by swelling, in the presence of such organic solvents or other organic fluids to which they are exposed. In most applications, a low non-specific adsorption is desirable to avoid compromising the purity of recovered ligate; the membranes of the invention are particularly advantageous in this respect, as the subject polyamides are substantially non-hydrophobic, a common source of non-specific adsorption in conventional affinity membranes. The size of the polymers is not critical; number average molecular weights of from about 15,000 to about 35,000 daltons are exemplary. Higher molecular weight polyamides (for example above about 20,000 daltons) are particularly useful when purity of product is an objective, as this reduces the number of terminal carboxyl and amino groups in the membrane; while the terminal amino groups are employed according to the invention as activation sites, which can be amplified as desired, terminal unblocked carboxyl groups are potential ion-exchange sites, and may contribute to undesirable non-specific adsorption. Many such aliphatic polyamide films or hollow fibers are known in the art for other uses, and are exemplified by, inter alia, the non-aromatic polyamide films or hollow fibers described in U.S. Pat. Nos. 4,340,480 (to Pall, issued July 20, 1982); 4,340,479 (to Pall, issued July 20, 1982); 4,595,503 (to Schindler, et al., issued June 17, 1986); or 4,482,514 (to Schindler, et al., issued Nov. 13, 1984); U.S. Pat. No. 3,876,738 (to Marinaccio, issued Apr. 8, 1975); U.S. Pat. No. 4,247,498 (to Castro, issued Jan. 27, 1981); U.S. Pat. No. 4,519,509 (to Castro, issued May 28, 1985); each incorporated herein by reference. Particularly interesting polyamide films comprise polycaprolactams, especially the various nylons such as nylon 6, 66, 610, 612, and 666.

The number of activatable primary amino groups (i.e., $-NH_2$ groups) present in the starting polyamide microporous membrane are important, as it is these groups which comprise the activation sites of the starting polyamide; preferred starting microporous membranes include those wherein the polyamide components have an average number of activatable primary amino groups of at least about 20 $\mu m$ $NH_2$ per gram polyamide. Alternatively, the number of activatable primary amino groups on a starting polyamide microporous membrane having fewer than the desired activation sites can be increased as desired to obtain an amplified polyamide membrane suitable for use in the present invention. For example, acid hydrolysis of a starting polyamide microporous membrane under conditions which do not substantially alter the morphology of the starting membrane, particularly with respect to pore size and porosity, will provide additional activatable primary amino activation sites. Other techniques which increase the number of activatable primary amino groups present in the starting membrane, without substantial disruption of its integrity, are also useful for increasing the number of starting polyamide activation sites.

In one aspect of the invention, the primary amino activation sites of the starting or amplified polyamide membrane are activated to obtain a matrix according to the invention, and the selected ligand is then directly bound to these sites. If desired, the starting or amplified membrane activation sites may be activated according to the invention and first reacted with a spacer molecule such as an alkylenediamine (e.g., $H_2N-(CH_2)_n-NH_2$ wherein n is from about 1 to 5) to provide an amino-terminal "leash" bound to the membrane to improve access of ligate to bound ligand as discussed in more detail below; in this event, the terminal amino group of the spacer molecule becomes an activation site on the starting membrane. In another aspect of the invention, the primary amino activation sites on either the starting or amplified polyamide material are activated according to the invention, and a polyhydroxyl-containing material such as a polysaccharide is covalently bonded to the starting polyamide membrane by reaction of the activated sites with a portion of the free hydroxyl groups of the polyhydroxyl material under similar nondisruptive conditions to form a composite membrane comprising a hydrophilic layer bonded to the starting polyamide membrane. Remaining free hydroxyl groups on the polyhydroxy layer are then activated according to the invention to form the corresponding composite matrix, and the selected ligand is bound to the activated hydroxyl groups. In the former instance, acid hydrolysis and similar methods directly amplify the polyamide starting membrane by increasing the number of activatable primary amino groups on the membrane. In the latter instance, the starting membrane is indirectly amplified by the polyhydroxyl-containing material, which functions to increase the total number of activation sites to increase ligate density potential on the product affinity membrane and space the ligand binding site from the membrane to improve spatial access of ligate to bound ligand. The hydrophilic layer of the composite membrane also functions to shield any ion-exchange sites present on the membrane from target ligates.

Suitable polyhydroxy materials for amplification of the polyamide starting membrane comprise substantially water-soluble oligomers or polymers containing a plurality of hydroxyl groups reactive with activated amino groups on the starting polyamide membrane and activatable according to the process of the invention to bind ligand to form a stable, uncharged composite matrix as described above under conditions which do not destabilize the starting membrane, the polyhydroxy material, or the ligand. Preferred oligomers/polymers are branched-chain compounds wherein the branches (leashes) carry free hydroxyl groups distal to the backbone of the polymer and function as spacers between the body of the matrix and activatable hydroxyl groups for binding ligand; as known in the art, such spacer chains or arms promote access of bound ligand to ligate, and are particularly useful when affinity is dependent on complementary stereochemical configurations of ligate and ligand macromolecules. Many such compounds are known for this use in conjunction with affinity separation matrixes; particularly suitable hydroxyl-containing materials for use in the present invention comprise, for example, natural polysaccharides, particularly natural hexose-based polysaccharides. Polyglucose, dextran, starches, cellulose, gums such as glucans or xylans, or chemical derivatives thereof, such as hydroxyethyl cellulose, are exemplary. For purity of product, polysaccharides which do not introduce ion-exchange sites onto the membrane, such as chitosan, are especially useful. Hydroxyl content of the materials is selected to provide a sufficient number of hydroxyl groups reactive with activated amino groups of the starting polyamide membrane to form the composite membrane, and to provide a sufficient number of additional activatable hydroxyl groups to afford a desired number of activation sites on the composite membrane for subsequent activation to form the composite matrix of the invention for binding of ligand. Increases in activation sites on the starting membrane by up to about 500% or more are contemplated with introduction of hydroxyl groups according to the invention.

2. Preparation of Matrix

Matrices according to the invention are prepared from the starting membranes described above by activation of sites on the membrane (either hydroxyl or amino activation sites) followed by binding of selected ligand to the activated site. Activators useful for this purpose are selected for reactivity with the amino groups present on the starting membrane, which optionally contains amino-terminal leashes, or for reactivity with the hydroxyl groups present on the composite membrane, and for activation of these sites to promote reactivity of the membrane with the selected ligand. In general, any ligand reactive with an activated site to bind ligand to membrane as further described below is suitable for use in conjunction with the activators to provide the affinity membrane of the invention. To form the matrix, a compound reactive with the primary amino activation sites of the polyamide microporous membrane (directly amplified or "leashed" if desired) or the hydroxyl groups of the composite membrane, which activates the membrane for binding of selected ligand (herein referred to as "activator") is reacted with the starting membrane. The activator residue (i.e., that portion of the activator introduced into the membrane during the reaction) promotes reaction of the ligand with the matrix activated sites during ligand binding and may either be wholly displaced with direct linkage of ligand to membrane, or be only partially displaced during ligand binding with formation of a bridging group between ligand and matrix. That is, the ligand may either completely replace the activator residue during binding of the ligand, or react with and bind to the activator residue.

Activators according to the invention comprise activators which react with both membrane and ligand under conditions which do not substantially impair the function of the membrane as an affinity membrane; which do not substantially reduce theoretical affinity of the ligand for the ligate; which promote yield and purity of product; which are soluble in solvents that do not substantially affect membrane characteristics, particularly pore dimensions or porosity; which are not significantly subject to unwanted side reactions; and which provide useful ligate binding sites (i.e., ligand bound to the activated membrane sites functions to bind ligate). Further, activators which form a bridging group to the ligand preferably are readily reactive with ligand, and react with the membrane and ligand to provide linkages between matrix and ligand which are substantially stable and uncharged; activators which are to be replaced by ligand comprise those capable of forming residues bound to the membrane which are good leaving groups, easily displaced by the ligand under conditions nondisruptive to the membrane. Activators for binding ligands or leashes containing nucleophilic groups such as amino, thiol, or hydroxyl groups, particularly polyamide or protein ligands, include those which provide a) stable and uncharged (non-ionic)

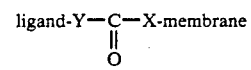

linkages such as ureylene

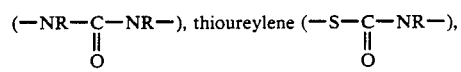

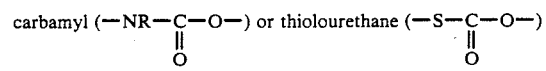

linkages between membrane and ligand; b) stable and uncharged —NR— (amino), —S— (thioether), or —O— (ether) direct linkages between membrane and ligand, and c) stable and uncharged cyanuric chloride

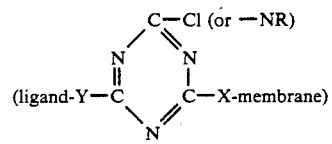

linkages between membrane and ligand; wherein X is O or NR; Y is a nucleophilic residue, particularly NR, O, or S; and R is H or substituted or unsubstituted alkyl, typically from about $C_1$-$C_5$-alkyl. In the above-noted linkages, "ligand-Y-" refers to linking moieties derived, for example, from amino, thiol, or hydroxyl reactive groups on the ligand, rather than from the activator or from the membrane; other corresponding linkages Y within the scope of the invention are obtainable from other nucleophilic ligands, wherein Y is the nucleophilic residue. "-X-membrane" refers to membrane linkages wherein the linkage X is derived from either amino or hydroxyl activation sites on the membrane. Exemplary useful activators within the scope of the above for activating activation sites on the starting polyamide or composite polyamide membrane with subsequent binding of selected ligand include 1,1'-carbonyldiimidazole (CDI) or a reactive derivative thereof which forms a corresponding monoimidazole residue on reaction with the membrane and is partially displaced by a reactive nucleophilic ligand; 2- fluoro-1-methyl-pyridinium$^{(+)}$ toluene-4-sulfonate$^{(-)}$ (FMP) or a reactive derivative thereof which loses a fluorine atom on membrane activation and is completely displaced by a reactive nucleophilic binding ligand; and trichlorotriazine (CyCl$_3$) or a reactive derivative thereof, particularly a dichlorotriazine derivative as described more fully below, which loses one chlorine atom on activation of the membrane and loses another on reaction with a reactive nucleophilic ligand, all as illustrated in the following Examples. While CDI is quite reactive and especially useful for that reason, other reagents which yield stable and uncharged linkages are also useful, such as substituted aromatic or aliphatic chloroformates; p-nitrophenyl-chloroformate, N-hydroxysuccinimide chloroformate, or trichlorophenyl-chloroformate are exemplary. As known in the art, these chloroformates may be employed to link a nitro-functional or hydroxyl-functional residue to the membrane; the nitro group may then be reduced to provide an additional amino activation site and both the hydroxyl and amino chloroformate residues may be subsequently activated as described herein. Additional chlorotriazines useful in the process of the invention include Cy(NR)Cl$_2$, wherein R is alkyl as defined above.

The specified activators are selected for chemical reactivity, excellence of product, and economy; equivalent reactants which serve the above-stated ends with the same economy of purpose are useful.

3. Activation of Matrix

In general, activation of the matrix is preferably carried out employing organic solvents, as many of the activators described above, such as CDI and FMP, may be water-labile; acetone, dioxane, cyclohexane, chlorofluorocarbons such as a FREON (DuPont Chemical Corp., Wilmington Del.), and acetonitrile are suitable; dimethylsulfoxide (DMSO) may also be used, but undesirable changes in membrane morphology may result if it is used substantially above room temperature. Activation is accomplished according to standard chemical techniques well-understood by those skilled in the art.

Depending on the membrane and/or ligand employed, activation conditions will vary; however, particularly in the case of CyCl$_3$ which is very reactive, it is recommended that activation be carried out anhydrously; in the case of CyCl$_2$ trichlorotriazine derivatives, it is recommended that the reaction be carried out under basic conditions, such as at a pH from about 6.5 to 9.5, most particularly from about 8.0 to about 8.5. These conditions promote displacement of a single chloride from the chlorotriazine activator, resulting in a stable bond between the matrix and the chlorotriazine residue. Preferably, a first chlorine atom is initially displaced from trichlorotriazine by reaction with the starting membrane in aprotic solvent in the presence of an acceptor for product HCl, such as a tertiary amine; matrix-bound CyCl$_2$ is then conveniently reacted with the ligand in an aqueous carbonate/bicarbonate system to displace an additional chlorine atom and bind the ligand. To ensure that the remaining halogen does not provide a charged site conducive to non-specific binding, it is desirable to block this site, as by reaction of the ligand-bound matrix with an alkanolamine, such as ethanolamine. Alternatively, the trichlorotriazine is first derivatized to eliminate a first active chlorine atom as described below under Examples.

Ligands useful in the invention comprise ligands broadly useful in affinity separations having affinity for a target ligate which are reactive with the above-described activated sites on the polyamide matrix to form a ligate binding site, i.e., a site where the ligand is chemically bound and biologically active to bind ligate.

Ligands for use in purifications according to the present invention include both ligands which biospecifically interact with complementary target ligates (commonly termed "affinity purification", or "immunoaffinity purification" in antibody/antigen systems) and ligands which ionically interact with target counterions, for example by van der Waals attraction (commonly termed "ion-exchange purification") are contemplated. Preferably, the ligand has a high affinity for the ligate and, for optimum isolation and purification of the ligate, a high biospecificity; these properties should not be substantially impaired when the ligand is bound to the matrix, e.g., it should not be substantially altered chemically by the coupling procedures described herein or sterically by its orientatation to the matrix when affinity is dependent on spatial orientation of ligate and ligand. The ligand is generally selected for ability to insolubilize the ligate from the parent biological fluid, and to form with the ligate a readily dissociable non-disrupting complex if isolation and concentration of the ligate is desired.

As noted above, particularly contemplated ligands include those containing nucleophilic groups reactive with sites activated with CDI, FMP, or a di- or trichlorotriazine to bind ligand, especially nucleophilic primary or secondary amino groups, thiol groups or hydroxyl groups; or, alternatively, carboxyl-terminal ligands reactive with the above-described amino-terminal leashes, for example by using an aqueous catalyst as understood in the art. Most particularly, such ligands comprise those suitable for affinity purification of biological macromolecules, especially proteins or glycoproteins, including enzymes; hormones; growth factors such as EGF and FGF; immunoglobulins including monoclonal and polyclonal antibodies; antigens; lectins; Protein A; Protein G; lymphokines including interferons and interleukins; blood components, for example erythropoietins or platelet factor, or plasma components such as fibrin, fibrinogen, fibronectin, thrombins, thromboplastins, prothrombins, or Factors VII–XIII, especially VIII and IX. Ligands suitable for use in affinity purification of nucleic acids, particularly RNA and DNA; and cells may also be bound to the matrix of the invention. Ligands having affinity for target ligates in such purifications are well-known in affinity chromatography, and any such ligands, including those obtained from genetically engineered organisms, which include groups reactive with activated sites on the matrix of the invention to form ligate binding sites as described herein are contemplated. Exemplary affinity pairs used in conventional affinity separation procedures include antigen/complementary antibody; protein A/immunoglobulin; lectin/oligosaccharide; hormone/complementary receptor; enzyme/complementary substrate analogues; inhibitor/complementary dye; nucleic acid/histone; all these systems are useful in the present invention. Ligands useful for plasmapheresis with the affinity membrane of the invention particularly include ligands adapted for removal of pathological proteins from blood plasma, especially pathological immunoglobulins characteristic of autoimmune disease. Ligands of particular interest in such applications include Proteins A and G which have biospecificity for immunoglobulins such as IgG and IgM, and immunoglobulins adapted for isolation and recovery of Proteins A and G from biological fluids (such as recombinant systems) for use as ligands in other purifications according to the invention. Clinical therapeutic and diagnostic applications are particularly contemplated.

Ligand attachment to the polyamide matrix is conveniently carried out in an aqueous environment or in an organic solvent system, as required to solubilize the selected ligand; providing that the system does not denature or destabilize the matrix or ligand, a number of systems (for example DMSO/water) will prove satisfactory without interfering with ligand attachment.

The degree of attachment of ligand (i.e., number of bound ligands) to activated sites is dependent on several factors, including ligand/ligand and ligand/activator interactions, e.g., charge and steric effects. Addition of small ligands to the composite membrane appears to be somewhat dependent upon the amount of indirect amplification with the polyhydroxyl material, i.e., the number of activated hydroxyl groups present for binding with the ligand; larger ligands such as BSA (bovine serum albumin) do not appear to have this dependency to any significant degree. Degree of attachment will also vary with the nature of the polyamide starting material, and the activator employed. An excessive number of ligands is to be avoided as this may lead to crowding, particularly with large ligands, and interfere with ligate recovery. The affinity membrane may be used in any convenient form for the combined affinity purifications and filtrations described above. Particularly contemplated forms are those which have a cross-flow geometry, such as hollow fiber membranes. Systems which operate under pressure (e.g., up to about 5 bar) are of especial interest. Membranes having a thickness of from about 10 to about 200μ, especially for use in pressurized systems, are particularly suitable. The membranes may be encased in a housing such as a syringe, cartridge, or centrifuge tube to facilitate traverse of the filtrate through the membrane, typically under pressure, as known in the art.

EXAMPLES

Methods and Materials

In the following Examples, the polyamide starting membranes used were a pure polycaprolactam (nylon 6) membrane commercially available as polyamide "386" and a sulphonic acid derivative commercially available as polyamide "390" (Akzo, Fiber and Polymer Div., D5600 Wuppertal, Federal Republic of Germany). The pure polycaprolactam in the Examples below is preferred for isolation and purification of ligates, as the sulphonic acid derivative may introduce non-specific binding sites into the membrane via the sulphonic acid residues. CDI, FMP, and $CyCl_3$ were commercially obtained from Sigma Chemical, St. Louis Mo., U.S.A. (CDI) and Aldrich Chemical, Milwaukee Wis., U.S.A. (FMP and CyCl). Polyglucose M 100 was obtained from Grain Processing Corp., Muscatine, Id., U.S.A. $CyCl_3$ derivatives wherein one of the chlorines is replaced (leaving two reactive chlorine atoms) to form a starting material can readily be employed in place of the $CyCl_3$ exemplified, particularly $CyCl_2NR$, wherein one of the chlorine atoms has been replaced by an alkylamine NR, for example wherein R is $C_1$–$C_5$-alkyl, to form the corresponding N-alkyl derivative of $CyCl_3$; or wherein one of the chlorine atoms has been replaced by an alkanolamine NR, for example wherein R is hydroxy-substituted $C_1$–$C_5$-alkyl, especially ethanolamine, to form the corresponding N-hydroxyalkyl derivative; such reactions are exemplary of Ciba dyestuff chemistry which is directed to forming reactive dyes such as Cibachrome dyes (e.g., Cibachrome 37A, Ciba-Geigy Corp., Basel, Switzerland) for use in dyeing common substrate materials, and which have also proved useful in binding ligates such as BSA to an affinity substrate.

EXAMPLE 1

Amplification of Activation Sites on Polyamide Membrane by Acid Hydrolysis.

The starting membrane (nylon 386 or 390) was hydrolyzed with 1N HCl for 72 hrs at room temperature (@RT). (Similar hydrolyzation conditions, e.g., 1N HCl @ 45° C., 2N HCl @RT, 3.5N HCl @RT, or comparable strengths of formic acid for comparable periods of time gave similar results). Increase in amino activation sites was assayed by standard ninhydrin reaction. Results are shown in Table I. It is apparent that acid hydrolysis substantially increased the number of primary amino groups present on the membrane. The chemical and mechanical integrity of the membrane was maintained.

TABLE I

| Fiber | $\mu M\ NH_3/g$ fiber |
|---|---|
| Native 386 nylon | 36 |
| Acid hydrolyzed 386 nylon | 178 |
| Native 390 nylon | 44 |
| Acid hydrolyzed 390 nylon | 234 |

EXAMPLE 2

Preparation of Composite Membrane (Activation of Polyamide)

A. The starting polyamide membrane (nylon 386 or 390) was activated with cyanuric chloride ($CyCl_3$) with 1% $CyCl_3$ in an acetone/triethylamine solvent system (a non-aqueous basic system) for 15 min to 16 h at RT to activate primary amino groups of the membrane according to the following scheme:

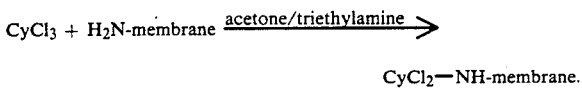

$$CyCl_3 + H_2N\text{-membrane} \xrightarrow{acetone/triethylamine}$$

$$CyCl_2\text{—NH-membrane}.$$

Polyglucose M-100 was then reacted with the activated membrane to covalently link the polysaccharide with the polyamide membrane to form a composite membrane according to the following scheme: $CyCl_2$—NH-membrane + polyglucose-$CH_2OH$ →polyglucose-$CH_2O$—CyCl—NH-membrane. Both chemical and mechanical integrity of the product composite membrane remained intact.

B. The procedure of Example 2A was repeated, employing either starch or dextran as the polysaccharide, with similar results.

C. The procedure of Example 2A was repeated, employing either CDI or FMP as the activator instead of $CyCl_3$, with comparable results.

As set forth in Table 2, polysaccharide (polyglucose M-100) addition in these experiments was quantitated (neutral sugar assay was performed by standard phenol sulfuric DuBois assay). Amplification of the polyamide membrane is reported in terms of $\mu M$ glucose/g of polyamide. Based on the introduction of glucose moieties, greatest amplification was achieved when the membrane was dried with acetone, activated with $CyCl_3$. (referred to in the Table as CyCl), washed with acetone and reacted with polyglucose (Experiment #1 of Table 2).

TABLE 2

| Introduction of Polyglucose Hydroxyl Groups | |
|---|---|
| Fiber | μM Glucose/g Fiber |
| Native 386 nylon | 1.0 |
| Native 390 nylon | 0.9 |
| 386-CyCl + M 100 (#1) | 203 |
| 390-CyCl + M 100 (#1) | 294 |
| 386-CDI + M 100 | 125 |
| 390-CyCl + M 100 | 143 |
| 386-CDI + M 100 | 56 |
| 390-CDI + M 100 | 37 |
| 386 + M 100-CDI | 12 |
| 390 + M 100-CDI | 20 |
| 386-CyCl + M 100 | 160 |
| 390-CyCl + M 100 | 43 |
| 386-CyCl + dextran | 68 |
| 390-CyCl + dextran | 84 |
| 386-CyCl + M 100 | 24 |
| 390-CyCl + M 100 | 20 |
| 386 + M 100-CDI | 12 |
| 386-CDI + M 100 | 17 |
| 386 + M 100-CDI | 6 |
| 386-CDI + M 100 | 7 |
| 386 + M 100-FMP | 9 |
| 386-FMP + M 100 | 16 |

EXAMPLE 3

Activation of Polyamide Membrane or Composite Polyamide Membrane with CDI

A. CDI (1,1'-carbonyldiimidazole) was reacted in non-aqueous solvent for from about 15 to 20 minutes at RT with the starting or amplified polyamide membrane and the polyglucose composite membrane from Example 1 or 2, above, according to the following scheme to provide an activated matrix for ligand binding:

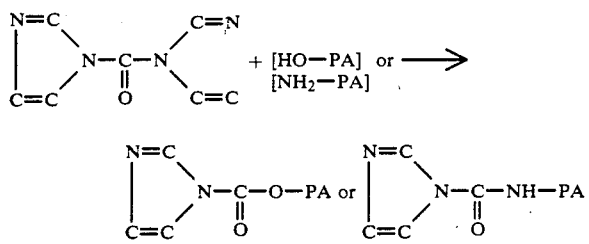

wherein PA is polyamide, HO—PA is the composite membrane of Example 2, and NH$_2$—PA is the starting polyamide membrane or amplified PA membrane of Example 1.

B. The remaining imidazole ring was then replaced with a NH$_2$-terminal ligand as described in Example 4C below according to the following scheme to provide a urethane or urea linkage:

[ligand-NH$_2$] ⟶

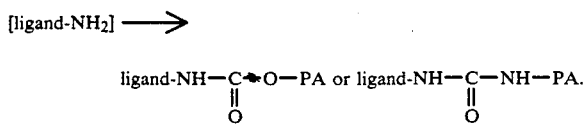

Corresponding schemes wherein ligand-NH$_2$ is ligand-Y and Y is a nucleophilic group as described above such as —OH, —SH, or —NHR are also within the scope of the invention.

EXAMPLE 4

Activation of Polyamide of Composite Polyamide Membrane with CyCl$_3$

Both the starting or amplified polyamide membrane from Example 1 and the composite polyglucose membrane from Example 2, above, were activated with cyanuric chloride according to the following scheme:

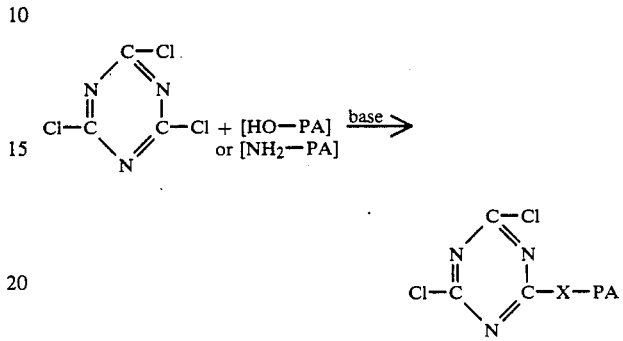

wherein PA is polyamide, HO—PA is the composite membrane of Example 2, NH$_2$—PA is the starting polyamide membrane or the amplified membrane of Example 1, and X is —O— or —NH—, corresponding to the reacting membrane.

A. Activation of Starting Polyamide Membrane with CyCl$_3$

The membrane was activated according to the activation procedure described in Example 2 for preparation of the composite membrane.

B. Activation of Composite Membrane with CyCl$_3$

The membrane was activated according to the activation procedure described in Example 2 for preparation of the composite membrane.

EXAMPLE 5

Activation of Polyamide or Composite Polyamide Membrane with FMP

Both the starting or amplified polyamide membrane from Example 1 and the composite polyglucose membrane from Example 2, above, were activated with FMP according to the following scheme:

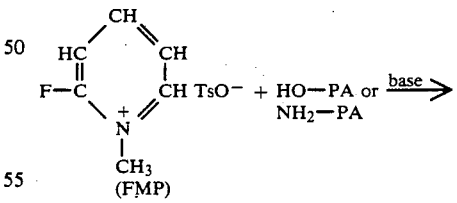

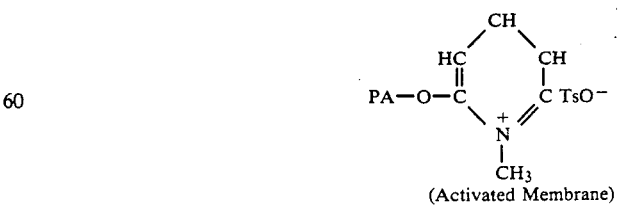

Ligand-Y wherein Y was —NH$_2$ was then reacted with the membrane-bound 1-methyl-pyridinium toluene-4-sulfonate according to the following scheme:

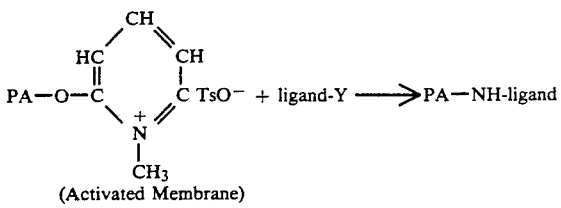

(Activated Membrane)

EXAMPLE 6

Attachment of Ligand to Polyamide Membrane

A. Attachment of Lysine to CyCl$_3$ Activated Membranes

The activated membranes of Example 4 were rinsed with solvent and exposed to a nucleophilic ligand (lysine, obtained from Sigma) dissolved in bicarbonate buffer for 2-24 h at RT or 4° C., depending upon the experiment. Unbound ligand was removed by rinsing with one or more of the following: bicarbonate buffer, ethanolamine in bicarbonate buffer, sodium acetate buffer, distilled water, or phosphate buffered saline. The membrane lysine content was assayed by ninhydrin assay (above). Binding ligand displaced one of the remaining dichlorotriazine chlorine atoms according to the following scheme:

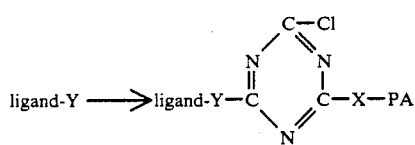

wherein X, Y, and PA are as defined above.

Remaining active chlorine atoms were blocked to diminish possible sites for non-specific binding by exposing the ligand-bound membrane to 2-aminoethanol solution at pH>8.5 overnight (the last chlorine is slowly reactive).

B. Attachment of Lysine to CyCl$_3$, CDI or FMP Activated Membrane

Ligand (lysine) was attached to the CyCl$_3$—, CDI—, or FMP-activated membranes of Examples 1, 3, 4 and 5 above, as described in Example 4C. In experiments 6A and 6B, lysine was selected as an exemplification of a small ligand molecule having ready accessibility to membrane activated sites with low steric hindrance. Results of lysine addition to CDI, CyCl$_3$, and FMP activated membranes are summarized in Table 3:

TABLE 3

| | ATTACHMENT OF THE LIGAND LYSINE | | |
|---|---|---|---|
| | Polyamide | mg lys/gPA | μ NH$_3$/gPA |
| 386 | Native | 3.5 | 24 |
| 390 | Native | 4.1 | 28 |
| | Solvent | | |
| | A     B | | |
| 386 | CDI/CDI | 13.8 | 94 |
| 390 | CDI/CDI | 17.0 | 186 |
| 386 | CDI/CDI | 2.3 | 16 |
| 390 | CDI/CDI | 3.5 | 24 |
| 386 | CyCl/CDI | 38.0 | 224 |
| 390 | CyCl/CDI | 12.0 | 84 |
| 386 | CyCl/CyCl | 11.9 | 81 |
| 390 | CyCl/CyCl | 18.9 | 121 |
| 386 | CyCl/CDI | 5.3 | 36 |
| 390 | CyCl/CDI | 98.5 | 144 |
| 386 | CyCl/CyCl | 15.0 | 102 |

TABLE 3-continued

| | ATTACHMENT OF THE LIGAND LYSINE | | |
|---|---|---|---|
| | Polyamide | mg lys/gPA | μ NH$_3$/gPA |
| 390 | CyCl/CyCl | 19.0 | 330 |
| 386 | CyCl/CDI | 13.7 | 93 |
| 390 | CyCl/CDI | — | — |
| 386 | CyCl/CDI | 16.1 | 110 |
| 390 | CyCl/CDI | 15.2 | 104 |
| 386 | CyCl/CDI | 0.6 | 4 |
| 390 | CyCl/CDI | 2.0 | 14 |
| 386 | CyCl/CyCl | 0.9 | 6 |
| 390 | CyCl/CyCl | 1.9 | 13 |
| 386 | CDI indirect/CDI | 15 | |
| 390 | CDI direct/CDI | 14 | |
| 386 | FMP direct/FMP | 9 | |
| 386 | FMP direct/FMP + urea wash | 4 | |
| 386 | FMP indirect/FMP | 4 | |
| 386 | FMP indirect/FMP + urea wash | 4 | |

C. Attachment of BSA (bovine serum albumin) to CyCl$_3$, CDI or FMP Activated Membrane BSA was attached as ligand as described in Example 6A for lysine. Membrane BSA content was assayed by standard bicinchoninic acid method. BSA illustrates the accessibility and binding of larger molecules to the membrane of the invention. Results of BSA addition to CDI, CyCl$_3$, and FMP activated membranes are summarized in Table 4:

TABLE 4

| | ATTACHMENT OF THE LIGAND BSA | | |
|---|---|---|---|
| | Polyamide | mg BSA/gPA | μ BSA/gPA |
| 386 | Native | 2.4 | 0.036 |
| 390 | Native | 0.2 | 0.003 |
| | Solvent | | |
| | A     B | | |
| 386 | CDI/CDI direct | 12.6 | 0.19 |
| 390 | CDI/CDI indirect | 18.0 | 0.27 |
| 386 | CDI/CDI indirect | 10.3 | 0.16 |
| 390 | CDI/CDI indirect | 9.5 | 0.14 |
| 386 | CyCl/CDI | 12.4 | 0.19 |
| 390 | CyCl/CDI | 12.8 | 0.19 |
| 386 | CyCl/CyCl | 11.0 | 0.17 |
| 390 | CyCl/CyCl | 12.5 | 0.11 |
| 386 | CyCl/CDI | 11.6 | 0.18 |
| 390 | CyCl/CDI | 11.5 | 0.17 |
| 386 | CyCl/CyCl | 10.1 | 0.15 |
| 390 | CyCl/CyCl | 12.4 | 0.19 |
| 386 | CyCl/CDI | 10.7 | 0.16 |
| 390 | CyCl/CDI | 10.8 | 0.16 |
| 386 | CyCl/CDI | 12.4 | 0.19 |
| 390 | CyCl/CDI | 10.9 | 0.16 |
| 386 | CyCl/CDI | 12.3 | 0.19 |
| 390 | CyCl/CDI | 11.5 | 0.17 |
| 386 | CDI direct/CDI | | 0.19 |
| 390 | CDI indirect/CDI | | 0.19 |
| 386 | FMP direct/FMP | | 0.29 |
| 386 | FMP direct/FMP + urea wash | | 0.28 |
| 386 | FMP indirect/FMP | | 0.24 |
| 386 | FMP indirect/FMP + urea wash | | 0.24 |

D. Attachment of Cibacron Blue Dye to CYCl$_3$, CDI or FMP Activated Membrane

Cibacron Blue Dye was attached as ligand to a CyCl$_3$-generated polyamide composite membrane and a CDI-generated polyamide composite membrane; both the composite membranes were then activated with CDI to provide activation sites for the dye, as described above. Cibacron Blue Dye was also attached as ligand to a CDI-activated polyamide membrane as described above.

E. Attachment of Lectin (Con A) to a CDI-generated Polyamide Composite Membrane (Example 2C above)

post-activated with CDI and a CDI-activated Starting Membrane (Example 3, above)

The activated membrane was rinsed and exposed to Con A lectin (Sigma Chemical) which was dissolved in bicarbonate buffer and incubated overnight at RT. Unbound ligand (lectin) was removed the following morning by rinsing with one or more of the following: bicarbonate buffer, ethanolamine in bicarbonate buffer, sodium acetate buffer, distilled water, or phosphate buffered saline. Bound membrane lectin was assayed by the bicinchoninic acid method (above).

EXAMPLE 7

Affinity Exchange

A. Recovery of BSA

The affinity membrane of Example 6D (Cibacron Blue) was employed to recover BSA. The membrane was incubated with 1% BSA (Sigma Chemical) for 2 to 24 hr at RT or 4° depending upon the experiment, followed by elution of the membrane with 2M NaCl. Recovery of BSA was quantitated by the bicinchoninic acid method (above) as 0.10–0.17 $\mu$M BSA/g membrane with a mean value of 0.14 as the result.

B. Recovery of Glucose

The affinity membrane of Example 6D was employed to recover glucose, demonstrating utility of the membrane in the recovery of sugar-containing plasma membranes.

The Con A-affinity membrane was equilibrated with a) 0.1 M acetate (pH 6) containing 1M NaCl, 1mM $CaCl_2$, 1mM MgClphd 2, and 1mM $MnCl_2$; and b) 1.0 M NaCl/0.05 M phosphate buffered saline. $^3$H-glucose was made up in solution (b) and exposed to the Con A-membrane. The membrane was rinsed with solution (b). The rinsed membrane was eluted with 0.1 M $\alpha$-methyl-D-glucoside in 1M NaCl/0.05 M phosphate buffered saline.

What is claimed is:

1. A composite membrane for affinity separation comprising a polyamide microporous film covalently bonded to a polysaccharide, and further including a ligand adapted for affinity separation bound to the composite membrane.

2. The membrane of claim 1, wherein the microporous polyamide film comprises a polymer or copolymer of a caprolactam.

3. The membrane of claim 1, wherein the microporous polyamide film is a nylon.

4. The membrane of claim 1, wherein the ligand is bound linked to a site on the membrane activated with an activator selected from the group consisting of 1,1'-carbonyldiimidazole, 2-fluoro-1-methyl-pyridinium$^{(+)}$ toluene-4-sulfonate$^{(-)}$, trichlorotriazine, and reactive derivatives thereof.

5. The composite membrane of claim 1, wherein the polysaccharide is bound to the polyamide microporous film via a carbamyl, amino, substituted amino, or cyanuric chloride linkage.

6. The composite membrane of claim 1, wherein the ligand is bound to the membrane via a ureylene, thiol-ourethane, ether, thioether, amino, substituted amino, or cyanuric chloride linkage.

7. The composite membrane of claim 1, wherein the polysaccharide is a polyglucose, dextran, or starch.

8. A composite matrix for the immobilization of a ligand useful in an affinity separation or a compound useful in ion-exchange chromatography comprising a microporous polyamide film including activation sites activated with an activator and covalently bound to a polyhydroxyl compound to form the composite matrix.

9. The matrix of claim 8, wherein the average pore size of the polyamide film is from about 0.6$\mu$ to 3$\mu$.

10. The matrix of claim 8, wherein the polyhydroxyl activation sites on the composite matrix are activated to promote binding of the ligand to the matrix.

11. The matrix of claim 10, wherein the activator is selected from the group consisting of 1,1'-carbonyldiimidazole, 2-fluoro-1-methyl-pyridinium$^{(+)}$ to toluene-4-sulfonate$^{(-)}$, and trichlorotriazine, and reactive derivatives thereof.

12. The matrix of claim 11, wherein the activator is 1,1'-carbonyldiimidazole or a reactive derivative thereof.

13. The matrix of claim 11, wherein the activator is 2-fluoro-1-methyl-pyridinium$^{(+)}$ toluene-4-sulfonate$^{(-)}$ or a reactive derivative thereof.

14. The matrix of claim 11, wherein the activator is trichlorotriazine or a reactive derivative thereof.

15. The matrix of claim 10, adapted for the affinity purification of a biological fluid.

16. The matrix of claim 10, wherein the ligand is adapted for affinity purification of blood plasma.

17. The matrix of claim 8, wherein the polyhydroxyl compound is an oligomer or polymer.

18. The matrix of claim 8, wherein the polyhydroxyl compound is a polysaccharide.

19. The matrix of claim 18, wherein the polysaccharide is a natural hexose.

20. The matrix of claim 18, wherein the polysaccharide is a gum, a sugar, dextran, or a starch.

21. The matrix of claim 8, wherein the polyhydroxyl compound is a polyglucose, dextran or starch.

22. The matrix of claim 8, wherein the polyamide is a polymer or copolymer of caprolactam.

23. The matrix of claim 22, wherein the polyamide is nylon.

24. The composite matrix of claim 8, wherein the polyhydroxyl compound is bound to the polyamide film via a carbamyl, amino, substituted amino, or cyanuric chloride linkage.

25. The matrix of claim 8, wherein the polysaccharide is polyglucose, and wherein the polyglucose is present in an amount of no more than about 3.2% by weight of the composite matrix.

26. The matrix of claim 25, wherein the polyglucose is present in an amount of no more than about 2.5% by weight of the composite matrix.

27. A method for the preparation of a composite matrix for the immobilization of a ligand useful in an affinity separation or a compound useful in ion-exchange chromatography comprising activating at least some of the activation sites of a microporous polyamide film with an activator, reacting the activated groups with a polyhydroxyl compound to covalently bind the polyhydroxyl compound to the polyamide film to form a composite matrix, and then activating the unreacted activation sites of the composite matrix with a same or different activator to promote binding of the ligand.

28. The method of claim 27, wherein substantially all the activation sites are activated.

29. The matrix of claim 27, wnerein the number of reactive amino groups of the polyamide film have been increased by acid hydrolysis of the polyamide film.

30. The method of claim 27, wherein the activator is selected from the group consisting of 1,1'-carbonyldiimidazole, 2-fluoro-1-methyl-pyridinium$^{(+)}$toluene-4-sulfonate$^{(-)}$, trichlorotriazine, and reactive derivatives thereof.

31. The method of claim 30, wherein the activator is trichlorotriazine or a reactive derivative thereof.

32. The method of claim 30, wherein the activator is 2-fluoro-1-methyl-pyridinium$^{(+)}$ toluene-4-sulfonate$^{(-)}$ or a reactive derivative thereof.

33. The method of claim 30, wherein the activator is 1,1'-carbonyldiimidazole or a reactive derivative thereof.

34. The method of claim 27, wherein the microporous polyamide film comprises a polymer or copolymer of a caprolactam.

35. The method of claim 34, wherein the microporous polyamide film is a nylon.

36. The method of claim 27, wherein the polyhydroxyl compound is an oligomer or polymer.

37. The method of claim 27, wherein the polyhydroxyl compound is a polysaccharide.

38. The method of claim 27, wherein hydroxyl compound is polyglucose, dextran, or starch.

39. The method of claim 27, wherein the ligand is adapted for affinity purification of blood plasma.

* * * * *